United States Patent
Igaki (10) Patent No.: US 7,070,615 B1
(45) Date of Patent: Jul. 4, 2006

(54) LINEAR MATERIAL FOR BLOOD VESSEL STENT AND BLOOD VESSEL STENT UTILIZING SAME

(75) Inventor: Keiji Igaki, 1-21, Wakakusa 2-chome, Kusatsu-shi, Shiga (JP) 525-0045

(73) Assignee: Keiji Igaki, Shiga (JP)

( * ) Notice: Subject to any disclaimer, the term of this patent is extended or adjusted under 35 U.S.C. 154(b) by 167 days.

(21) Appl. No.: 09/979,377

(22) PCT Filed: Mar. 13, 2001

(86) PCT No.: PCT/JP01/01983

§ 371 (c)(1),
(2), (4) Date: Jul. 16, 2002

(87) PCT Pub. No.: WO01/67990

PCT Pub. Date: Sep. 20, 2001

(30) Foreign Application Priority Data

Mar. 13, 2000 (JP) .............................. 2000-073983

(51) Int. Cl.
*A61F 2/06* (2006.01)

(52) U.S. Cl. .................................. 623/1.15

(58) Field of Classification Search ............ 606/108, 606/191, 192, 194, 195, 198; 623/1.1–1.22; 523/105–450; 604/530; 264/230

See application file for complete search history.

(56) References Cited

U.S. PATENT DOCUMENTS

| | | | |
|---|---|---|---|
| 5,145,945 A | 9/1992 | Tang et al. | |
| 5,310,865 A * | 5/1994 | Enomoto et al. | 528/361 |
| 5,423,885 A | 6/1995 | Williams | |
| 5,514,378 A * | 5/1996 | Mikos et al. | 424/425 |
| 5,527,337 A | 6/1996 | Stack et al. | |
| 5,578,046 A | 11/1996 | Liu et al. | |
| 5,980,564 A | 11/1999 | Stinson | |
| 5,981,619 A * | 11/1999 | Shikinami et al. | 523/113 |
| 5,984,963 A | 11/1999 | Ryan et al. | |
| 6,245,103 B1 * | 6/2001 | Stinson | 623/1.22 |
| 6,281,262 B1 * | 8/2001 | Shikinami | 523/105 |

FOREIGN PATENT DOCUMENTS

| | | |
|---|---|---|
| EP | 0 446 852 A2 | 9/1991 |
| EP | 0 894 505 A2 | 2/1999 |
| EP | 0 923 912 A3 | 6/1999 |
| JP | 4-220456 | 8/1992 |
| JP | 11-197252 | 1/1999 |
| JP | 11-57018 | 3/1999 |
| JP | 11-188109 | 7/1999 |

* cited by examiner

*Primary Examiner*—Vy Q. Bui
(74) *Attorney, Agent, or Firm*—Bell, Boyd & Lloyd LLC (57) ABSTRACT

The present invention includes a linear material used for a stent implanted in a blood vessel such as the coronary artery, and a blood vessel stent employing this linear material. The linear material is formed of a biodegradable polymer poly-(L-lactic acid) having a crystallinity, as measured by differential calorimetry, of 15 to 60%. The linear material is a monofilament having a diameter of 0.08 mm to 0.30 mm. This monofilament is shaped to a tubular structure used as the blood vessel stent.

5 Claims, 9 Drawing Sheets

LINEAR MATERIAL FOR BLOOD VESSEL STENT AND BLOOD VESSEL STENT UTILIZING SAME

BACKGROUND OF THE INVENTION

The present invention relates to a linear material used for a stent implanted in the blood vessel of e.g., the coronary artery, and to a blood vessel stent employing this linear material.

If stenosis is formed in the blood vessel of, e.g., the coronary artery, a so-called percutaneous transluminal angioplasty (PTA) is usually applied. The PTA is the operation of inserting a balloon forming portion annexed to the vicinity of the distal end of a catheter in the portion of the blood vessel suffering from stenosis, and of expanding the balloon forming portion to expand the portion of the blood vessel suffering from stenosis to improve the blood flow. Usually, a blood vessel stent is implanted to prevent re-stenosis of the blood vessel in the site of the PTA.

The stent serves to maintain the patency of the blood vessel for the required period, preventing re-stenosis in the site undergoing PTA.

Since it was reported that a metal stent is effective in treating ischemic heart disease, remarkable progress has been achieved in the clinical use of the coronary stent. The coronary stent is highly promising, not only in terms of its prophylatic effect against acute closure, but also in its long-term prevention of restenosis and its therapeutic effect against lesions for which PTCA is considered inadequate. Thus, the coronary stent is widely used in operations such as cardiac intervention.

Comparative clinical trials employing the angioplasty with only a balloon and in employing the angioplasty with both a balloon and a stent have shown that the rates of occurrence of the acute coronary closure and of re-stenosis are both lower when the angioplasty with both a balloon and a stent is employed. Metal stents are reliable in the short and mid-term results as disclosed in many reports. However, the possibility of unexpected events against, for example, the coronary artery has been pointed out in long term tests.

In a metal stent, there is no established standard therapeutic method against re-stenosis in the stent. For example, reapplication of PTCA on occurrence of re-stenosis in the stent (in-stent re-stenosis) may be one method envisaged. However, since the stent is already implanted and remains in the blood vessel, it becomes difficult to expand the balloon, thus obstructing the re-application of PTCA.

Where re-stenosis occurs over a long area or in multiple branches, a frequently-used method is that of implanting a number of metal stents side-by-side. By surgical thoracotomy, a by-pass operation for preserving blood flow by connecting a by-pass to the blood vessel so as to avoid the site of stenosis is an effective technique against in-stent re-stenosis. However, some metal stents do not show up easily in angiography and, if a metal stent remains implanted in the target portion where the bypass is to be connected, the bypass operation itself has to be abandoned. This is a significant burden for the patient.

Currently, investigations are underway as to the compatibility of blood flow and metal. Since metal is hydrophilic and tends to form the thrombus, the thrombus-forming properties of the metal stent pose a serious problem. Thus, for the purpose of prevention of thrombotic closure in the stent-implanted portion, a concentrated anti-thrombotic therapeutic operation is indispensable. However, there is always the associated risk of further hemorrhagic complications.

For these reasons, implanting a metal stent which will remain permanently in the body poses a problem.

The main objective of implanting a stent is to avoid acute coronary closure and to reduce the frequency of the occurrence of re-stenosis. It is reported that, since acute coronary closure and re-stenosis are phenomena that relate each other for a certain period, they require only temporary treatment. It is, therefore, desirable that the function of the stent may be maintained only for a required period such that the stent will not remain in the living body as foreign substance once its role has been fulfilled. In particular, since the increase in the rate of re-stenosis wanes after about six months, the function of the stent needs to be maintained during this six-month time period.

In view of the physical functions, the following properties are required of the stent:

(a) mechanical properties: such that, as the structural element, the stent needs to possess sufficient mechanical properties to keep the blood vessel open for a specified period of time; and (b) expansion/contraction properties: such that the stent diameter needs to be decreased during delivering to the target legion and to be increased up to a desired diameter at the target site of lesion; and (c) delivering capability: such that, the stent needs to be correctly implanted in the target legion of the coronary artery without migration, kinking, distortion or breakage.

SUMMARY OF THE INVENTION

It is an object of the present invention to provide a novel linear material used for a stent and a blood vessel stent which satisfy these requirements.

It is a more specific object of the present invention to provide a novel linear material used for a stent and a blood vessel stent having biodegradability, superior anti-thrombotic properties and a superior physical function, and which can be handled in the same manner as a metal stent.

The inventors of the present invention have conducted persistent investigations over a long period, whose results have led to the conclusion that, by selecting a biodegradable polymer poly-(L-lactic acid) for the stent material and by optimizing its crystallinity, the physical functions and biodegradability after a certain period may be made mutually compatible. The present invention has been completed on the basis of this information.

That is, the present invention provides a linear material for a blood vessel stent, wherein the linear material is formed of a biodegradable polymer poly-(L-lactic acid) with a crystallinity as measured by differential scanning calorimetry of 15 to 60%.

Moreover, the present invention provides a blood vessel stent formed by shaping a linear material into a tubular structure, in which the linear material is formed of a biodegradable polymer poly-(L-lactic acid) having a crystallinity as measured by differential scanning calorimetry of 15 to 60%.

The present blood vessel stent has an outer diameter of 2 to 5 mm, with the thickness of the linear material being 0.08 to 0.30 mm. It may be formed, for example, of a poly-(L-lactic acid) monofilament.

The poly-(L-lactic acid) is a biodegradable polymer which, when placed in the living body, is absorbed therein, disappearing after a pre-determined time period has elapsed.

The physical properties of this poly-(L-lactic acid) are significantly affected by the crystallinity. Moreover, the anti-thrombotic properties are also influenced by the crystallinity. By setting this crystallinity to 15 to 60%, the mechanical properties as well as the expansion/contraction capability and delivering capability are maintained. Furthermore, by setting the crystallinity to the above range, the stent formed by employing this linear material exhibits opening radial strength over a specified period, after which it swiftly disappears.

Additional features and advantages of the present invention are described in, and will be apparent from, the following Detailed Description of the Invention and the Figures.

DETAILED DESCRIPTION OF THE INVENTION

Referring to the figures, preferred embodiments of a linear material for a blood vessel stent and a blood vessel stent according to the present invention are explained in detail.

The linear material for a blood vessel stent according to the present invention is a filament-like product formed of poly-(L-lactic acid) and may be of any suitable configuration such as mono-filament or multi-filament. However, a monofilament configuration is preferable if the stent configuration as explained below is taken into account.

Although the monofilament diameter may be set arbitrarily, it may be limited, for example, by the size of the blood vessel stent for coronary arterial implantation. A blood vessel stent for coronary arterial implantation is 10 to 50 mm in length, formed to a tubular structure around 5 mm in diameter and contractible to roughly 2 mm for implantation into the blood vessel.

The monofilament constituting the blood vessel stent which may be thus contracted to a diameter of 2 mm must be no more than 0.3 mm in thickness. Moreover, the monofilament constituting the blood vessel stent requires a specific strength as explained below, and in order to be knitted or bent into a zig-zag shape to form a tubular structure, requires a specific rate of elongation and a specific elongation at rupture. In this respect, the monofilament of poly-(L-lactic acid) constituting a blood vessel stent of the above-mentioned dimensions, requires a thickness of not less than 0.08 mm in diameter.

Poly-(L-lactide), referred to below as PLLA, belongs to a biodegradable aliphatic polyester, and is chemically a polymer resulting from the dehydration condensation of lactic acid, and which is obtained on polymerization of an L-optical isomer of lactic acid only.

Although the weight average molecular weight of PLLA can be set arbitrarily so that it can be worked into a linear material, the weight average molecular weight is preferably not less than 55000. The mechanical properties are saturated at a weight average molecular weight not less than 55000, such that poly-(L-lactic acid) remains unchanged in its strength or modulus of elasticity if the molecular weight is increased beyond this value. Specifically, the weight average molecular weight of poly-(L-lactic acid) is 70000 to 400000 for practical application and preferably 100000 to 300000. In particular, if the monofilament is of a diameter of 0.08 to 0.30 mm, as described above, the weight average molecular weight is preferably not less than 100000.

If PLLA is considered as a biodegradable material, the rate of decomposition of PLLA is determined by the above-mentioned molecular weight, crystallinity and the diameter and surface area of the monofilament. In particular, in crystalline PLLA, the crystallinity and the diameter of the monofilament significantly affect the rate of decomposition.

When a blood vessel stent of tubular structure is formed using the PLLA monofilament and this stent is implanted in a blood vessel, strength is lowered accordingly with decomposition. In particular, when the crystallinity is low, the strength is greatly lowered and the speed of decomposition is fast. For this reason, there is a minimum limit for the crystallinity with regard to shape retention characteristics in that the stent retains the shape of the blood vessel over a predetermined period as it decomposes. As mentioned above, given that after implantation in a blood vessel, a six-month period of shape retention of the stent is required, the observational period of changes in the mechanical characteristics of the PLLA monofilament during decomposition was set at six months.

The inventors formed a stent as a tubular structure 10 to 50 mm in length as mentioned above and about 5 mm in diameter. In order to produce a blood vessel stent whose diameter may be contracted to about 2 mm for blood vessel insertion, PLLA monofilament with a diameter of 0.3 mm(A), 0.17 mm(B) and 0.08 mm(C) were produced. These PLLA monofilaments were immersed in 37° C. physiological saline for 6 months and their crystallinity and breaking loads were observed. The result as shown in FIG. 1 was obtained.

The breaking load of tantalum widely used in a metal stent is more than 6N. In a blood vessel stent using the PLLA monofilament, the blood vessel stent is formed as a tubular structure about 5 mm in diameter and 10 to 50 mm in length. The diameter of stent is contracted to about 2 mm for insertion into a blood vessel. Six months after implantation in the blood vessel of a blood vessel stent of the above formation, if a similar strength for maintaining the patency of the blood vessel to that of a metal stent is required, a breaking load of not, less than 6N is necessary. To achieve this, the crystallinity needs to be not less than 25% even for a monofilament A 0.3 mm in diameter, as is clearly shown in FIG. 1

A PLLA mono-filament with bio-absorbability is implanted into the body and, as it decomposes, the degree of crystallization rises. That is, the amorphous portion decomposes first.

Figure 1:
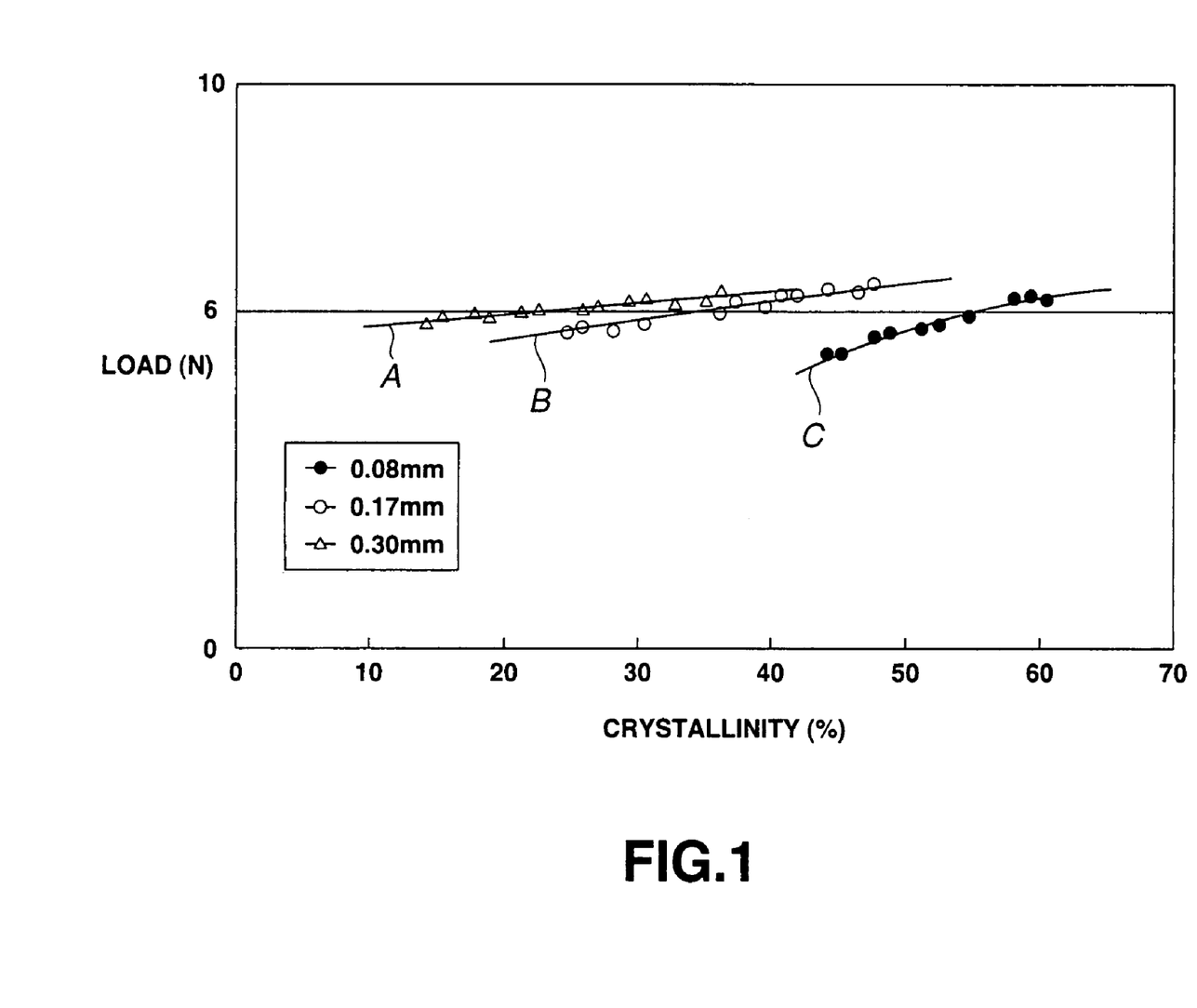
FIG. 1 is a graph showing the relationship between the crystallinity of the PLLA monofilament on immersion for six months in a 37° C. physiological saline and the breaking load.
Figure 2:
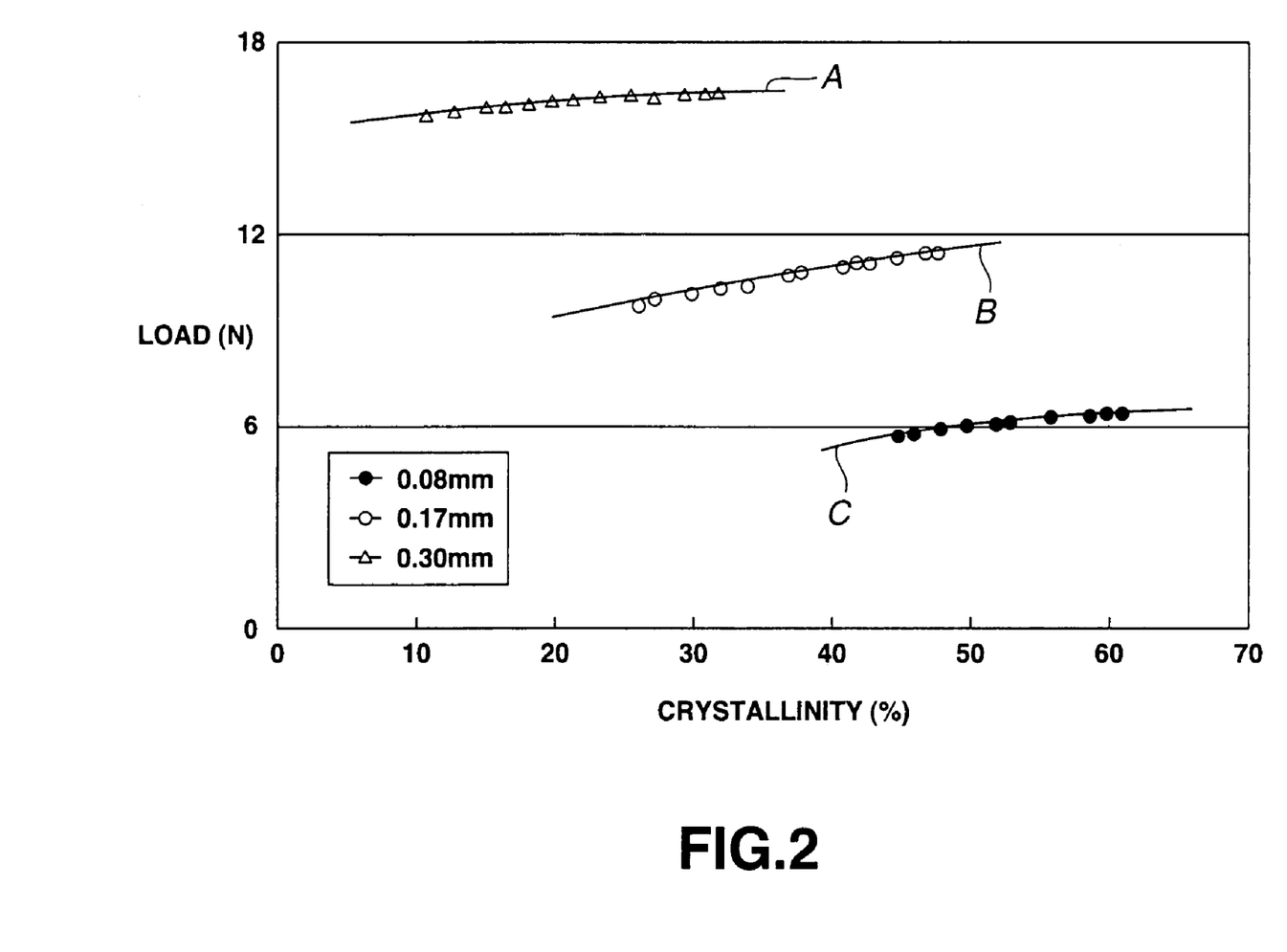
FIG. 2 is a graph showing the relationship between the crystallinity on formation of the PLLA monofilament and the breaking load.

The relation between the crystallinity and the load on formation of each of the monofilaments A, B, and C whose diameters are shown in FIG. 1, is shown in FIG. 2. That is, in the monofilaments A, each of which has a diameter of 0.3 mm, when immersed in a 37° C. physiolosical saline for six months, the 25% crystallinity required for a breaking load of not less than 6N was achieved. At the time of formation of the monofilaments, the crystallinity was about 15%.

From the results shown in FIGS. 1 and 2, supposing the maximum thickness of PLLA monofilament possible for forming a blood vessel stent of the above-mentioned dimensions, a minimum 15% crystallinity is required at the time of formation of the monofilament.

If application of the biodegradable polymer yarn to the blood vessel stent is considered, the PLLA to be used is required to display superior physical functions.

Thus, the optimum range of the PLLA crystallinity was investigated in terms of physical functions.

In view of the PLLA being a structural material of the blood vessel stent, such factors as the modulus of elasticity and strength (mechanical properties), ease of bending and workability (expansion/contraction performance) and ease of warping and flexibility (delivering performance) may be considered.

Of these, the modulus of elasticity and strength (mechanical properties) are most crucial. The modulus of elasticity and strength represent the factors relevant to the force with which the blood vessel is kept open by the stent as a structural member. Thus, the modulus of elasticity and strength are preferably equivalent or superior to those of the metal stent. In the case of the metal stent using tantalum wire, with a diameter of 126 μm, the breaking strength is approximately 6N, while the modulus of elasticity is approximately 50 GPa.

In order to achieve a strength equivalent or superior to that of a metal stent, the crystallinity of PLLA monofilament at time of formation needs to be not less than 15%, as explained above. The higher the crystallinity, the higher the strength. From this viewpoint, as high as possible a crystallinity is desirable.

However, if the crystallinity is increased, the elongation at rupture is lowered; that is, the PLLA becomes hard and brittle.

Of the afore-mentioned physical functions, ease of bending is required in view of the expansion/contraction and delivering capabilities. That is, a suitable elongation at rupture is required. For example, if a linear material is to be shaped into a stent, expansion/contraction performance is required. If the linear material is broken in the process, such material is totally useless.

If a blood vessel stent is formed with a length of 10 to 50 mm and thickness of 2 to 5 mm as mentioned above and processed as a cylindrical structure by knitting into a tubular shape or bending into a zig-zag shape, the monofilament employed as the linear material must be able to be curved or bent without cracking or rupturing during processing. In order to achieve this, although dependent on the diameter of the linear material, if a PLLA monofilament with a diameter of 0.08 to 0.3 mm is employed in order to form the blood vessel stent as described above, it has been revealed during the process of stent manufacture that not less than 15% elongation at rupture is required as curving or bending limit.

In addition, if the PLLA monofilament as described above measurements is investigated, it is found that the capacity of a curve or bend is influenced by the elongation at rupture and the elongation at rupture changes with the crystallinity.

Figure 3:
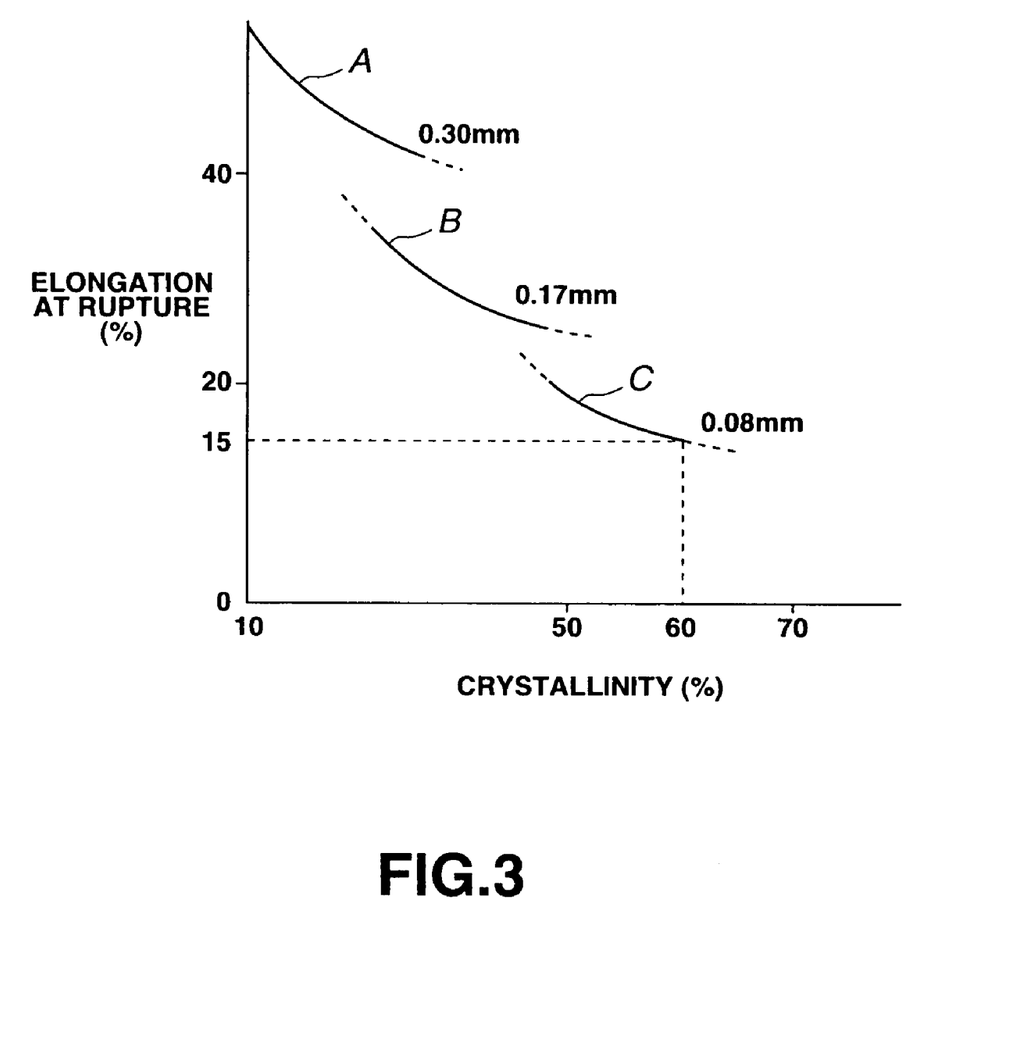
FIG. 3 is a graph showing the relationship between the crystallinity of the PLLA monofilament and the elongation at rupture.

FIG. 3 shows the relationship between the crystallinity and the elongation at rupture of A, B and C PLLA monofilaments with diameters of 0.30 mm, 0.17 mm and 0.08 mm, respectively. For each of the A, B and C monofilaments, the elongation at rupture changes according to the crystallinity as shown in FIG. 3. Therefore, to achieve a PLLA monofilament of not less than 15% of elongation at rupture for a diameter of 0.08 mm, the crystallinity must be 60% or less. Since in reality the PLLA monofilament at 60% or less crystallinity was actually hard and brittle, it broke easily and could not form the above-mentioned blood vessel stent.

The cross-sectional shape of the monofilament is arbitrary and may, for example, be circular or elliptical. However, as the rate of decomposition is affected by the surface and cross-sectional shape of the monofilament, and is proportionate to its surface area, the thickness of the monofilament, along with its crystallinity, need to be taken into consideration.

Among other properties required of the blood vessel stent are its anti-thrombotic properties. The anti-thrombotic properties of PLLA will now be examined.

Among the indices indicating the anti-thrombotic properties of a material, there is thrombocyte adhesiveness, obtained by measurement with the column method. The higher the thrombocyte adhesiveness of a material under investigation, the lower its anti-thrombotic properties become, such that the material is not suited as a stent material.

If the stent material is of a so-called micro-domain structure in which different properties or materials are arranged alternately, the thrombocyte adhesion may be suppressed to a certain extent. The micro-domain structure is such a structure in which the physical properties of the material differ in the micro-units. Segmented polyurethane is known among polymers structurally exhibiting anti-thrombotic properties.

In a high molecular weight polymer material, the higher the crystallinity, the less likely thrombocytic adhesion is to occur. However, this does not mean that a higher crystallinity is desirable.

The above-mentioned PLLA assumes the crystalline and amorphous micro-domain structure such that, in PLLA, the crystallinity is felt to be intimately related to the anti-thrombotic properties.

However, in PLLA having an excessively high crystallinity, it has been reported that decomposition products in the form of needle-like crystals tend to cause inflammation when these are left for a prolonged time in the body. Therefore, an excessively high crystallinity is preferably avoided on the grounds of safety.

To this end, the crystallinity of the PLLA used as the linear material for the blood vessel stent according to the present invention needs to be in a range from 15 to 60% at the time of formation of PLLA.

The configuration of the blood vessel stent formed of the PLLA monofilament is hereinafter explained.

First, the blood vessel stent produced on knitting the above-mentioned monofilament is discussed.

Since the blood vessel stent is basically produced by knitting a single yarn, it is possible to form a cylindrical or tubular shaped blood vessel stent which is more homogeneous than a woven fabric obtained by crossing the warp and weft.

Figure 4:
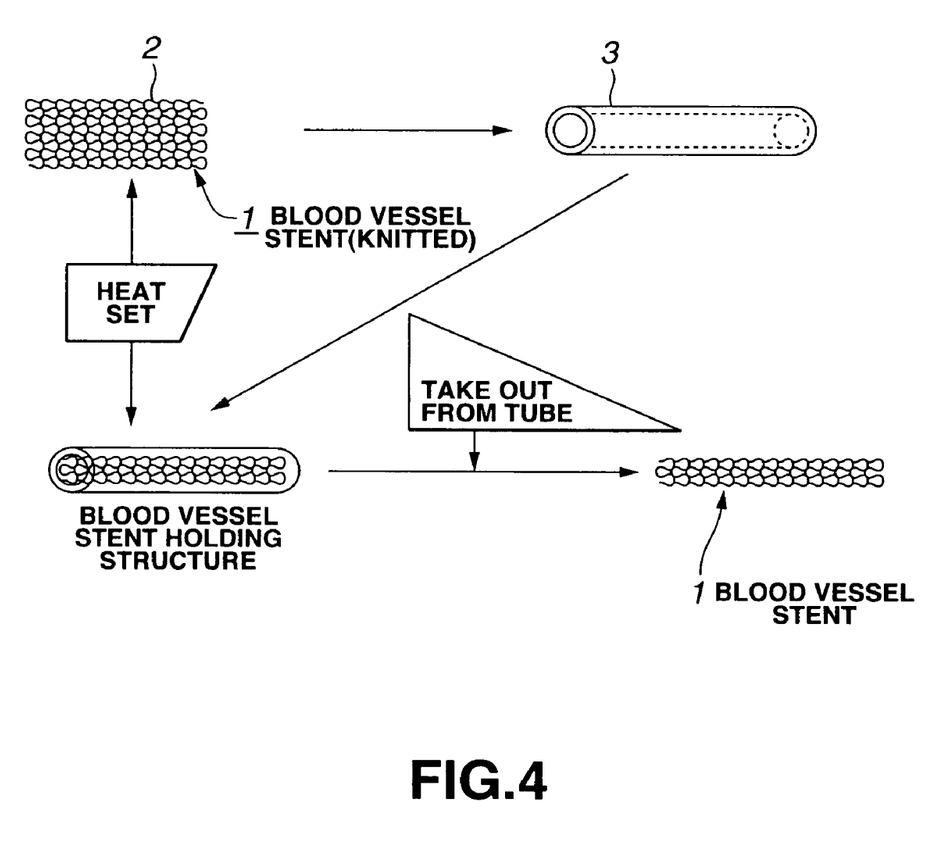
FIG. 4 is a schematic view showing the process of contracting a knitted blood vessel stent.

Moreover, this knitted blood vessel stent is able to pass through a meandering blood vessel to reach the target legion more easily than a metal stent or a stent formed by woven fabric. That is, the blood vessel stent formed by a knitted cloth exhibits trackability to any meandering and can be implanted in a bent portion of the blood vessel, and the knitted tubular stent has a strong expansion force wherein it is less likely to lose its hollow form. The knitted tubular blood vessel stent, with a diameter of approximately 5 mm, is heat-set by heat treatment to a diameter not larger than approximately 2 mm in order to insert and load the knitted tubular blood vessel stent in a blood vessel of finer diameter in the living body. This heat-setting process is shown in FIG. 4.

Figure 5:
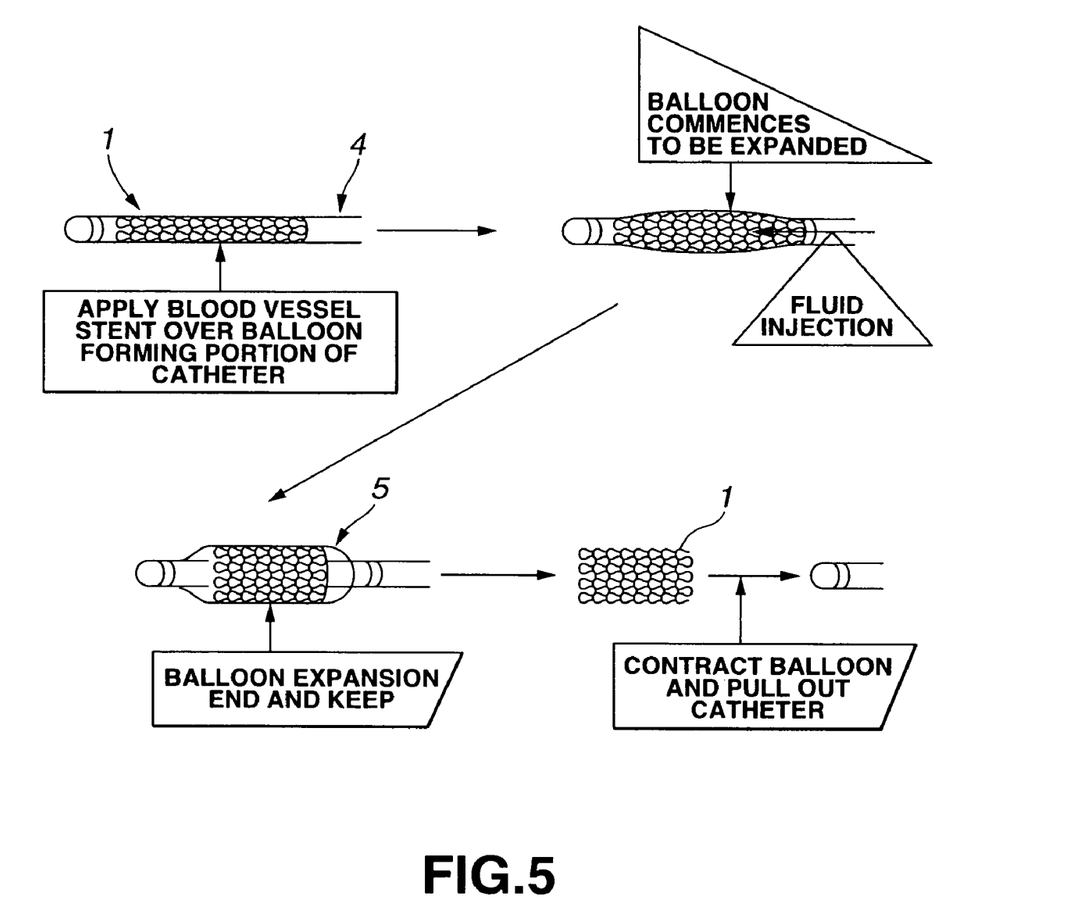
FIG. 5 is a schematic view showing the process of implantation of the knitted blood vessel stent into the blood vessel.

The process of implanting the heat-set blood vessel stent by catheter 4 having a balloon 5 in the blood vessel is shown conceptually in FIG. 5.

Figure 6:
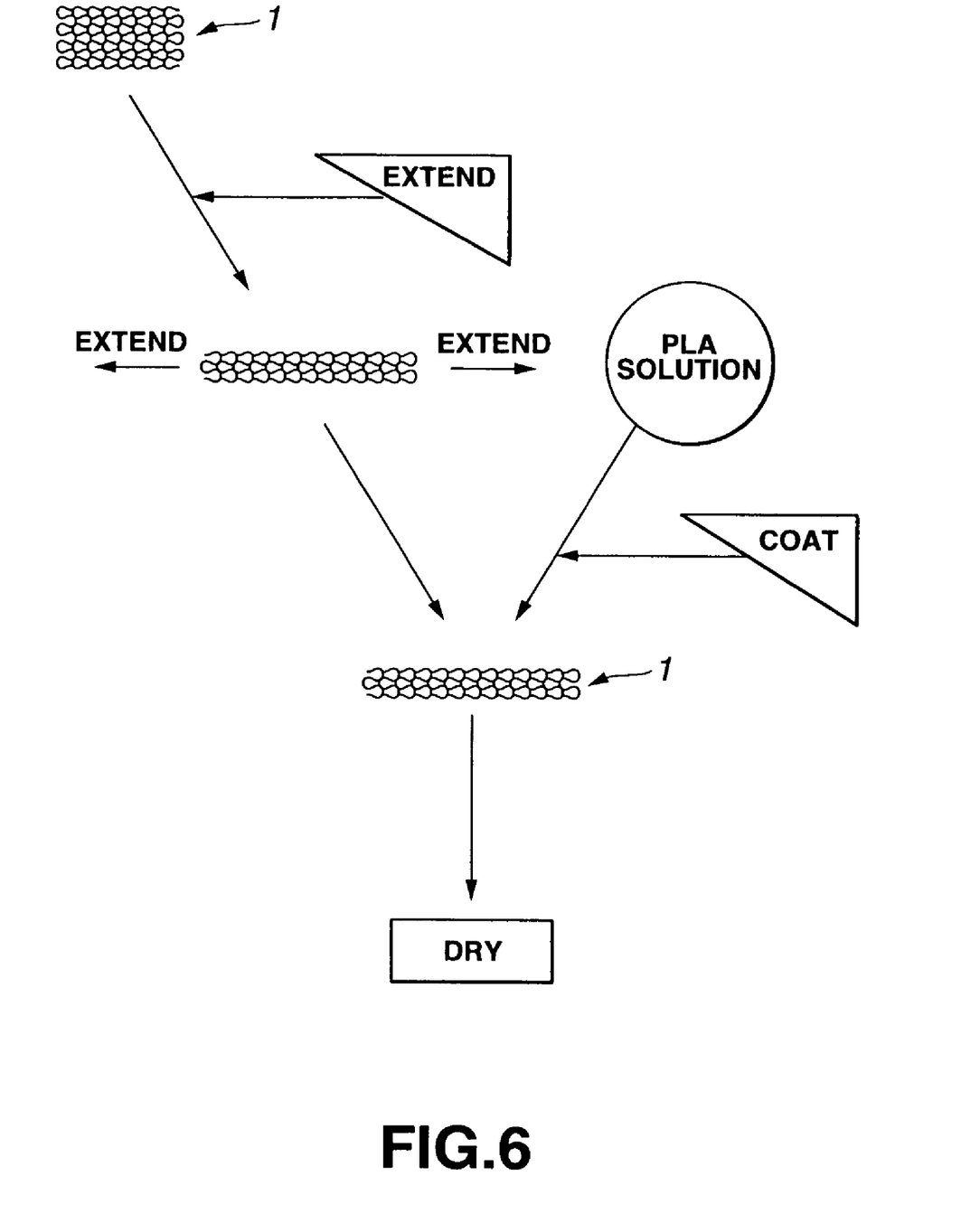
FIG. 6 is a schematic view showing an alternative method of contracting a knitted blood vessel stent.

An alternative method of contracting the blood vessel stent knitted from a PLLA monofilament is shown in FIG. 6. The advantage of the method shown in FIG. 6 is that, since a tube formed of a heat-resistant resin or metal is not used, the stent can be mounted directly on the balloon forming portion in the vicinity of the distal end of the catheter.

This blood vessel stent 1 is a blood vessel stent formed by knitting a PLLA yarn (PLLA monofilament 2) into cylindrical or tubular shape. This knitted cloth is superior to a woven cloth in softness and shape retention characteristics to other sorts of cloths, such as a felt-like non-woven cloth or a woven cloth formed by usual warp and weft yarns. This knitted blood vessel stent is further heat-set to exhibit more outstanding effects in softness and shape retention characteristics.

The tubular blood vessel stent 1, knitted from PLLA yarn, has a diameter of approximately 4 to 5 mm, and is implanted into a tube 3 of heat-resistant resin or metal with an inner diameter of approximately 1 to 3 mm; preferably, 2 mm. It is either subsequently heat-set, or heat-set during its gradual implantation in the tube 3. This yields a blood vessel stent heat-set to a diameter of approximately 2 mm (see FIG. 4).

If this process of heat setting is carried out when the knitted tubular blood vessel stent is of a relatively larger diameter, or the tubular member is heat-set when it is of a reduced diameter, the filament, yarn or loop at the terminal end of the knitted cloth shows good shape-retention performance, such that the heat-setting affords not only shape retention characteristics, but also minimizes the stress which the blood vessel stent would otherwise apply to the inner wall of the blood vessel of the living body.

The linear material, used for knitting the blood vessel stent of the present invention, can be made variable in its cross-sectional shape more easily than in the blood vessel stent formed of metal. That is, if the filament produced on spinning is of a hollow or profiled cross-section, or if a monofilament or multi-filament yarn is used, it is possible to control the affinity with the living body or its shape retention performance.

If, several months after the blood vessel stent of the present invention has decomposed and been absorbed into the tissue of the living body, re-stenosis occurs in the blood vessel, a blood vessel stent can be re-implanted and loaded in the same site in the blood vessel. This is because a biodegradable polymer is used.

Furthermore, if a thin sheet of a felt-like non-woven cloth, formed of the biodegradable polymer, and worked into a tubular shaped member, exhibits shape retention characteristics and elasticity comparable with those of the knitted blood vessel stent of the present invention, it may also be used in place of the knitted product.

A blood vessel stent 11, obtained on bending a PLLA monofilament into a zigzag shape which is subsequently formed into a cylindrical shape, is hereinafter explained.

Figure 7:
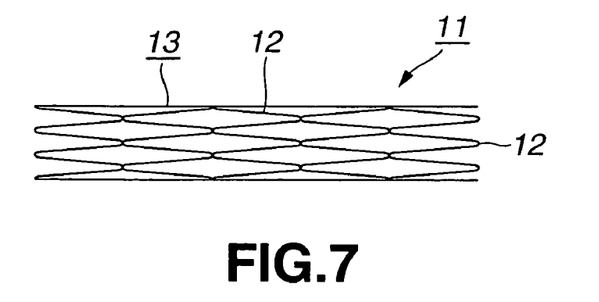
FIG. 7 is a schematic plan view showing an illustrative blood vessel stent obtained by shaping a zig-zag shaped PLLA monofilament into a cylindrical form.

This blood vessel stent 11 includes a main body portion of the stent 13, obtained on bending a PLLA monofilament 12 exhibiting shape memory properties into a zigzag shape, and subsequently forming the resultant product into a tubular shape, as shown in FIG. 7.

Figure 8:
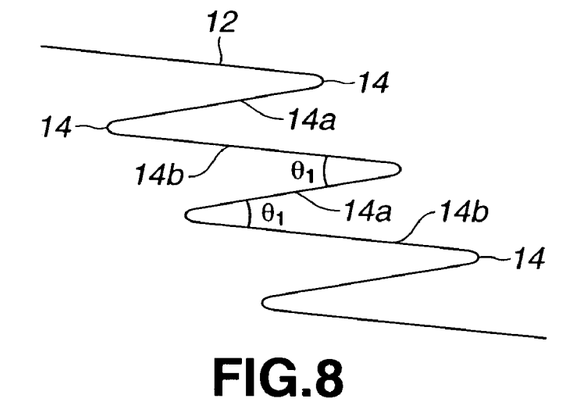
FIG. 8 is a schematic plan view showing the bent state of a monofilament constituting a main body portion of the stent.
Figure 9:
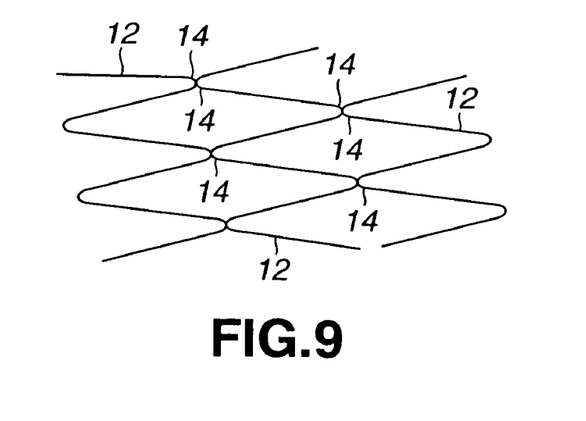
FIG. 9 is an enlarged plan view showing a portion of the main body portion of the stent.
Figure 10A:
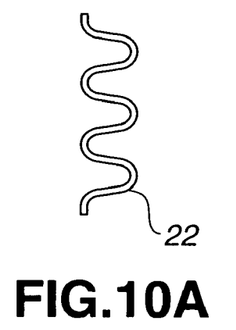
FIGS. 10A–10G are schematic views showing an illustrative PLLA monofilament in a non-woven non-knitted state.
Figure 10B:
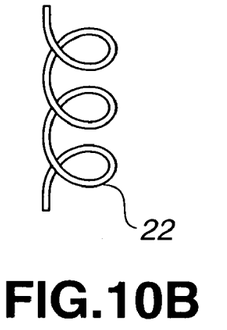
Figure 10C:
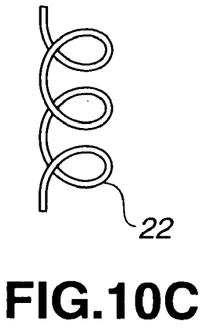
Figure 10D:
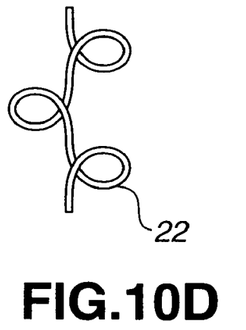
Figure 10E:
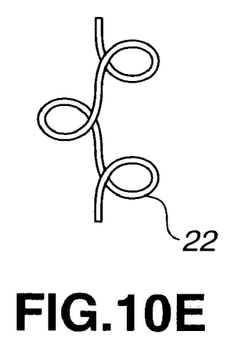
Figure 10F:
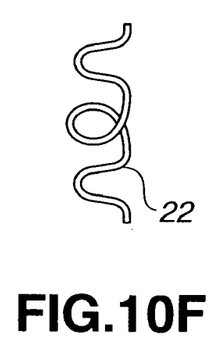
Figure 10G:
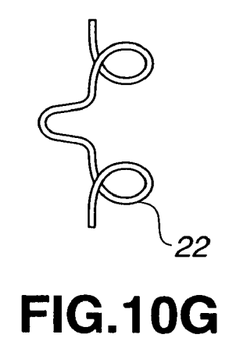

The PLLA monofilament 12 is coiled into a spiral shape, as it is bent into a zigzag shape to form consecutive vee shapes, to complete the main tubular body portion of the stent 13, as shown in FIG. 8. At this time, the monofilament 12 is wound spirally, with one side of the vee shape 14 being a short linear portion 14a and the other side being a long linear portion 14b. By having an approximately equal opening angle $\theta 1$ of the bent portions 14 formed in the monofilament 12, and by having approximately equal lengths of the short linear portions 14a and the long linear portion 14b, the apex points of the neighboring bent portions 14 come into mutual contact, as shown in FIG. 9. At least one part of the apex points of the neighboring bent portions 14 coming into mutual contact is bonded together. The monofilament 12, constituting the main body portion of the stent 13, retains its tubular shape by having the apex points of the bent portions 14 bonded together, as shown in FIG. 9.

The bent portions, having apex points which come into mutual contact, are bonded by heating and fusing the bonding portions to be bonded to a temperature not lower than the melting point Tm.

An embodiment in which the PLLA monofilament is formed into a stent in the non-woven non-knitted state is hereinafter explained.

Basically, this stent is processed by wrapping a single yarn without knitting or weaving around the periphery of a tubular or cylindrical member to form a tube tubular or cylindrical member. Specifically, as shown in FIGS. 10A to 10G, the PLLA monofilament 22 is allowed to meander or to form loops to form a planar mass of the PLLA monofilament 22. This planar article is then implanted around the peripheral surface of the tubular or cylindrical member to form a curvilinear shape.

Figure 11:
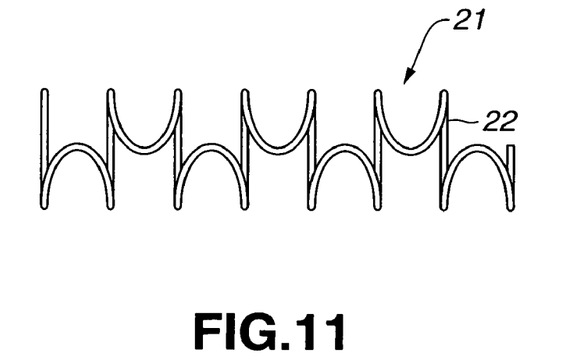
FIG. 11 is a schematic view showing an illustrative blood vessel stent obtained by shaping a PLLA monofilament in a non-woven non-knitted state into a cylindrical form.
Figure 12:
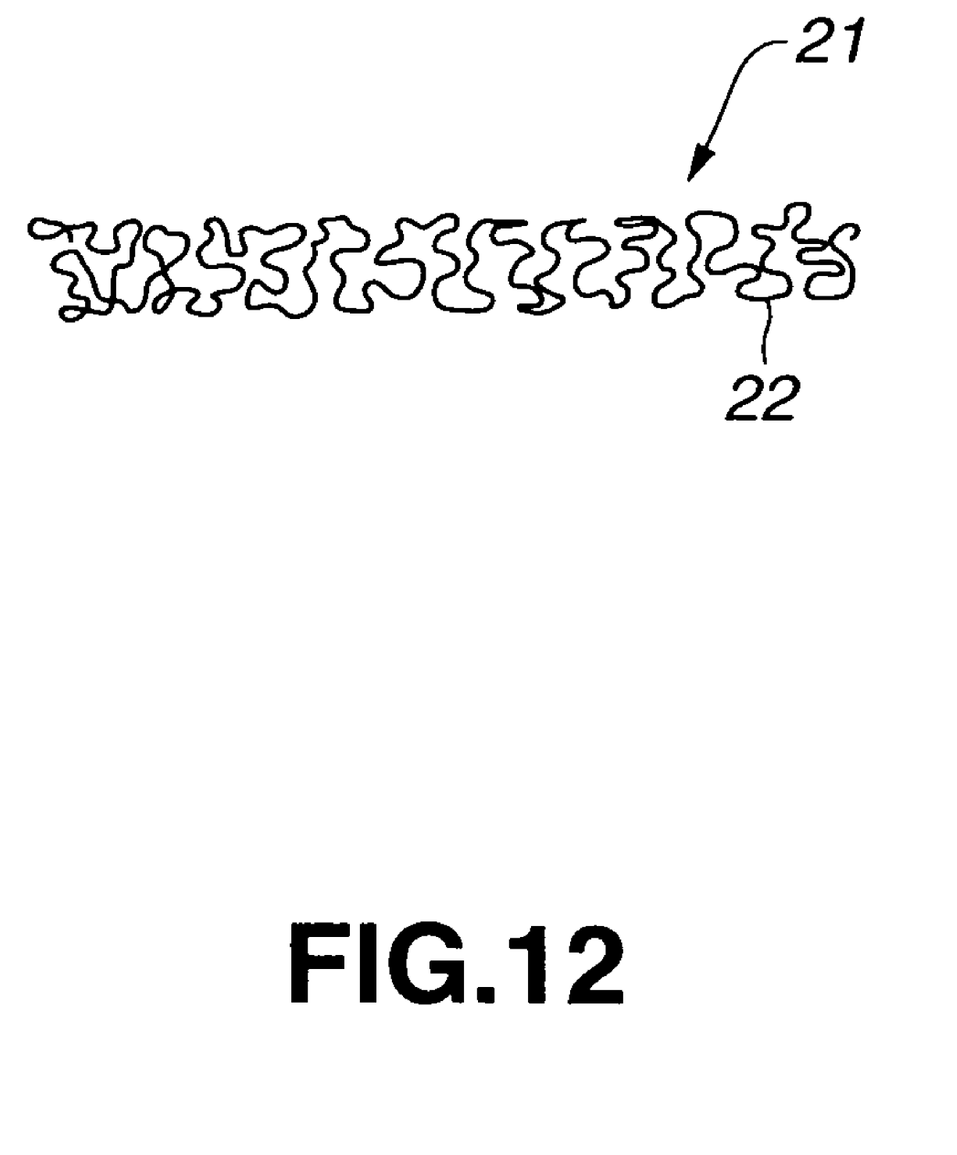
FIG. 12 is a schematic view showing another illustrative blood vessel stent obtained by shaping a PLLA monofilament in a non-woven non-knitted state into a cylindrical form.

FIG. 11 shows one such example for the blood vessel stent 21 in which the meandering PLLA yarn is formed into a tubular shape. FIG. 12 shows another instance of a blood vessel stent 21 in which the PLLA monofilament is formed into a stent in a non-woven non-knitted state. In a further instance, a looped PLLA monofilament 22 is shaped to a tube in a similar manner.

INDUSTRIAL APPLICABILITY

As is clear. from the above explanation, the present invention is able to offer a linear material for a blood vessel stent which has suitable absorbability and superior physical functions. By employing this material, it is possible to provide a blood vessel stent which exhibits opening radial strength over a predetermined period, after which it swiftly disappears.

Although the present invention has been described with reference to specific embodiments, those of skill in the art will recognize that changes may be made thereto without departing from the spirit and scope of the invention as set forth in the hereafter appended claims.

The invention claimed is:

1. A blood vessel stent comprising a linear material shaped into a tubular structure, the linear material being formed of a biodegradable polymer poly-(L-lactic acid) monofilament having a crystallinity as measured by differential scanning calorimetry of 15 to 60%.

2. A blood vessel stent as claimed in claim 1, wherein an outer diameter is 2 to 5 mm, and a diameter of said linear material is 0.08 to 0.30 mm.

3. A blood vessel stent as claimed in claim 1, wherein the monofilament is knitted to a tubular structure.

4. A blood vessel stent as claimed in claim 1, wherein the monofilament is bent to a zigzag shape and wound into a cylindrical shape to form the tubular structure.

5. A blood vessel stent as claimed in claim 1, wherein the monofilament, in a non-woven non-knitted state, is formed into a shape around the peripheral surface of a tubular structure.

* * * * *